US010058662B2

(12) United States Patent
Colomb

(10) Patent No.: US 10,058,662 B2
(45) Date of Patent: Aug. 28, 2018

(54) DEVICE FOR DISPENSING FLUID PRODUCT

(71) Applicant: APTAR FRANCE SAS, Le Neubourg (FR)

(72) Inventor: Arnaud Colomb, Verneuil sur Seine (FR)

(73) Assignee: APTAR FRANCE SAS, Le Neubourg (FR)

( * ) Notice: Subject to any disclaimer, the term of this patent is extended or adjusted under 35 U.S.C. 154(b) by 684 days.

(21) Appl. No.: 14/399,592

(22) PCT Filed: May 22, 2013

(86) PCT No.: PCT/FR2013/051111
§ 371 (c)(1),
(2) Date: Nov. 7, 2014

(87) PCT Pub. No.: WO2013/175121
PCT Pub. Date: Nov. 28, 2013

(65) Prior Publication Data
US 2015/0107590 A1 Apr. 23, 2015

(30) Foreign Application Priority Data

May 24, 2012 (FR) ..................................... 12 54799

(51) Int. Cl.
*A61M 15/00* (2006.01)
(52) U.S. Cl.
CPC .... *A61M 15/0058* (2014.02); *A61M 15/0021* (2014.02); *A61M 15/0045* (2013.01);
(Continued)
(58) Field of Classification Search
CPC ............ A61M 15/0021; A61M 15/025; A61M 15/0026; A61M 15/0033; A61M 15/0035;
(Continued)

(56) References Cited

U.S. PATENT DOCUMENTS

| 5,590,645 | A | 1/1997 | Davies et al. |
| 2009/0283095 | A1 | 11/2009 | Pocock et al. |

(Continued)

FOREIGN PATENT DOCUMENTS

| FR | 2 660 550 A1 | 10/1991 |
| FR | 2 936 425 A1 | 4/2010 |
| WO | 2006/079750 A1 | 8/2006 |
| WO | 2008/012458 A2 | 1/2008 |
| WO | 2009/007640 A1 | 1/2009 |
| WO | 2009/077700 A2 | 6/2009 |
| WO | 2009/136098 A2 | 11/2009 |
| WO | 2011/154659 A1 | 12/2011 |

OTHER PUBLICATIONS

International Search Report for PCT/FR2013/051111, dated Sep. 4, 2013.

*Primary Examiner* — Lynne Anderson
(74) *Attorney, Agent, or Firm* — Sughrue Mion, PLLC

(57) ABSTRACT

A fluid dispenser device including a body (10) and at least one cover element (11, 12) that is mounted to pivot on said body (10) between a closed position and an open position, said device including at least one individual reservoir containing a single dose of fluid, such as powder, opening means (80) being provided for opening an individual reservoir each time the device is actuated, said device including movable support means (50) that are adapted to move an individual reservoir against said opening means (80) on each actuation, said movable support means (50) being displaceable between a non-dispensing position and a dispensing position, said movable support means (50) being urged towards their dispensing position by resilient means (70), such as a spring or a spring blade, and being held in their non-dispensing position by blocking means that are released by the user inhaling, said device including a cocking member (800) that co-operates with said resilient means (70) and with a cam surface (51) that is formed on said movable support means (50), said cocking member (800) and said resilient means (70) being assembled in a housing provided in a housing piece (700) connected to a cover element (12).

10 Claims, 3 Drawing Sheets

(52) U.S. Cl.
CPC .... *A61M 15/0051* (2014.02); *A61M 15/0081* (2014.02); *A61M 15/0086* (2013.01); *A61M 15/0091* (2013.01); *A61M 15/004* (2014.02); *A61M 15/0008* (2014.02); *A61M 15/0026* (2014.02); *A61M 15/0036* (2014.02); *A61M 15/0043* (2014.02); *A61M 15/0071* (2014.02); *A61M 15/0073* (2014.02); *A61M 15/0075* (2014.02); *A61M 2202/064* (2013.01); *A61M 2205/19* (2013.01)

(58) Field of Classification Search
CPC ............ A61M 15/0036; A61M 15/004; A61M 15/0045; A61M 15/0051; A61M 15/0086

See application file for complete search history.

(56) References Cited

U.S. PATENT DOCUMENTS

| | | | |
|---|---|---|---|
| 2010/0175697 A1* | 7/2010 | Massot | A61M 15/0045 128/203.15 |
| 2010/0307492 A1* | 12/2010 | Fabien | A61M 15/0045 128/203.15 |
| 2010/0307493 A1* | 12/2010 | Kirniak | A61M 15/0045 128/203.15 |
| 2010/0319693 A1* | 12/2010 | Fagot | A61M 15/0045 128/203.15 |
| 2011/0120466 A1* | 5/2011 | Fagot | A61M 15/0045 128/203.15 |
| 2011/0168178 A1 | 7/2011 | Baillet | |
| 2013/0152928 A1* | 6/2013 | Kirniak | A61M 15/0045 128/203.15 |

* cited by examiner

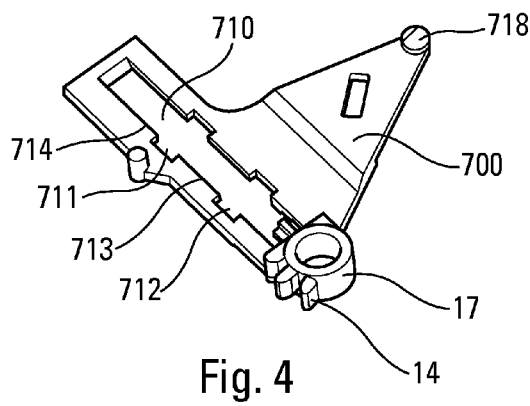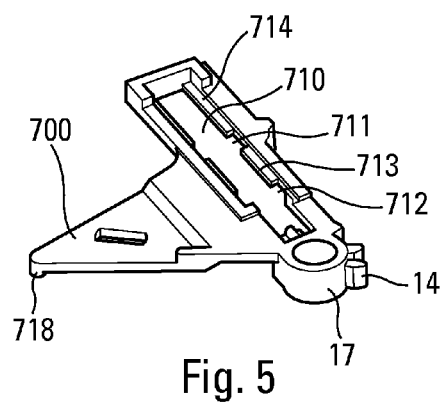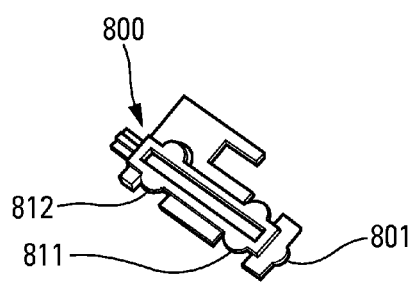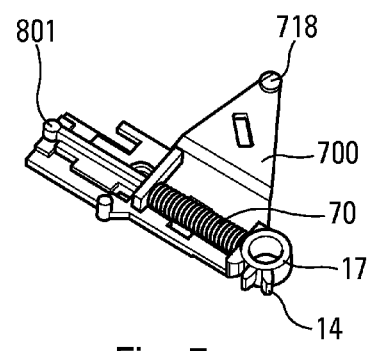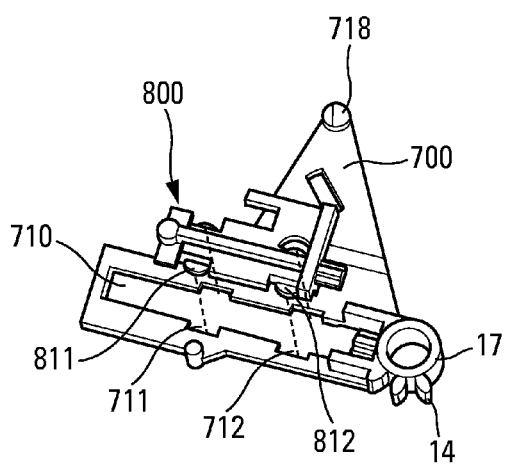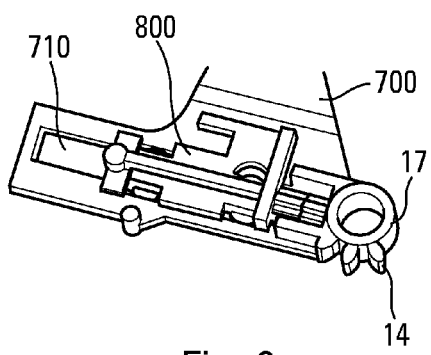

US 10,058,662 B2

DEVICE FOR DISPENSING FLUID PRODUCT

CROSS REFERENCE TO RELATED APPLICATIONS

This application is a National Stage of International Application No. PCT/FR2013/051111 filed May 22, 2013, claiming priority based on French Patent Application No. 1254799, filed May 24, 2012, the contents of all of which are incorporated herein by reference in their entirety.

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally initially loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the preceding dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. Another problem that may occur relates to assembling certain parts, in particular movable parts, that need to withstand large stresses in operation, and for which assembly needs to be particularly reliable so as to avoid any risk of malfunctioning. With the small size of certain parts, it can be complicated to guarantee such reliable assembly. Document WO 2008/012458 describes a prior-art device.

An object of the present invention is to provide a fluid dispenser device, in particular a dry-powder inhaler, that does not have the above-mentioned drawbacks.

In particular, an object of the present invention is to provide such a device that is simple and inexpensive to manufacture and to assemble, that can be assembled and used reliably, guaranteeing metering accuracy and reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

The present invention thus provides a fluid dispenser device including a body and at least one cover element that is mounted to pivot on said body between a closed position and an open position, said device including at least one individual reservoir containing a single dose of fluid, such as powder, opening means being provided for opening an individual reservoir each time the device is actuated, said device including movable support means that are adapted to move an individual reservoir against said opening means on each actuation, said movable support means being displaceable between a non-dispensing position and a dispensing position, said movable support means being urged towards their dispensing position by resilient means, such as a spring or a spring blade, and being held in their non-dispensing position by blocking means that are released by the user inhaling, said device including a cocking member that co-operates with said resilient means and with a cam surface that is formed on said movable support means, said cocking member and said resilient means being assembled in a housing provided in a housing piece connected to a cover element.

Advantageously, on each side, said housing includes side rails that are interrupted by side openings, said cocking member including side projections that are adapted to co-operate with said side openings so as to enable said cocking member to be assembled in said housing, said side rails co-operating with said side projections of said cocking member so as to enable said cocking member to slide in said housing, while holding said cocking member in said housing.

Advantageously, said side openings co-operate with said side projections solely in the assembly position of said cocking member, said resilient means urging said cocking member out of said assembly position.

Advantageously, said resilient means comprise a coil spring that is arranged in said housing.

Advantageously, said movable support means support a guide wheel, the reservoirs being made in the form of an elongate strip comprising a plurality of individual reservoirs disposed one behind another, said guide wheel causing said strip to advance each time the device is actuated.

Advantageously, said opening means include a perforator element that is adapted to cut a closure wall of the reservoir in such a manner that the cut portion(s) does/do not obstruct the opening(s) that is/are formed.

Advantageously, the device includes an inhalation piece and an inhalation trigger system that comprises a deformable air chamber that co-operates with said inhalation piece, and a trigger element that co-operates with said air chamber, such that during inhalation through said inhalation piece, said air chamber is deformed and said trigger element actuates said opening means, such that a reservoir is opened by said opening means.

These characteristics and advantages and others of the present invention appear more clearly from the following detailed description, given by way of non-limiting example, and with reference to the accompanying drawing, and in which:

FIGS. 4 and 5 are diagrammatic perspective views showing the housing piece, respectively from above and from below;

FIG. 6 is a diagrammatic perspective view from below of the cocking member;

FIG. 7 is a diagrammatic perspective plan view of the housing piece with the loader spring and the cocking member assembled in the housing;

FIGS. 8 and 9 are diagrammatic perspective views showing the assembly stage for assembling the cocking member in the housing of the housing piece, respectively before and after assembly.

Figure 1:
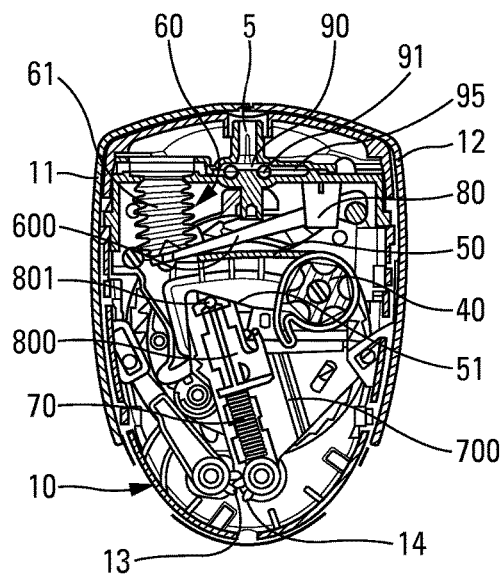
FIGS. 1 to 3 are diagrammatic section views of a dispenser device in an advantageous embodiment of the invention, respectively before opening, after opening but before inhalation, and after inhalation.
Figure 2:
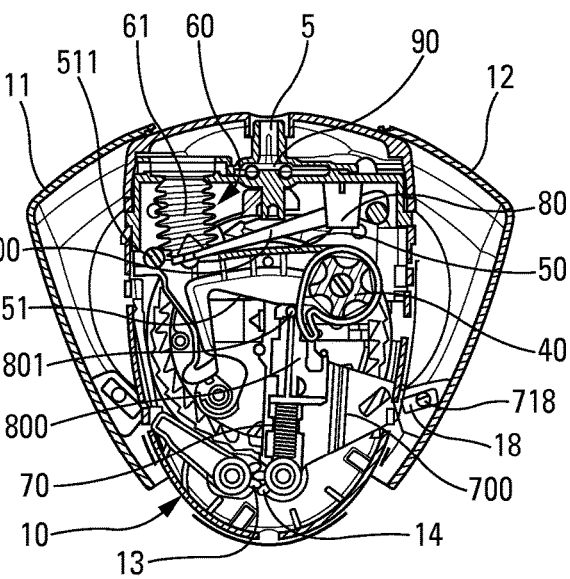
Figure 3:
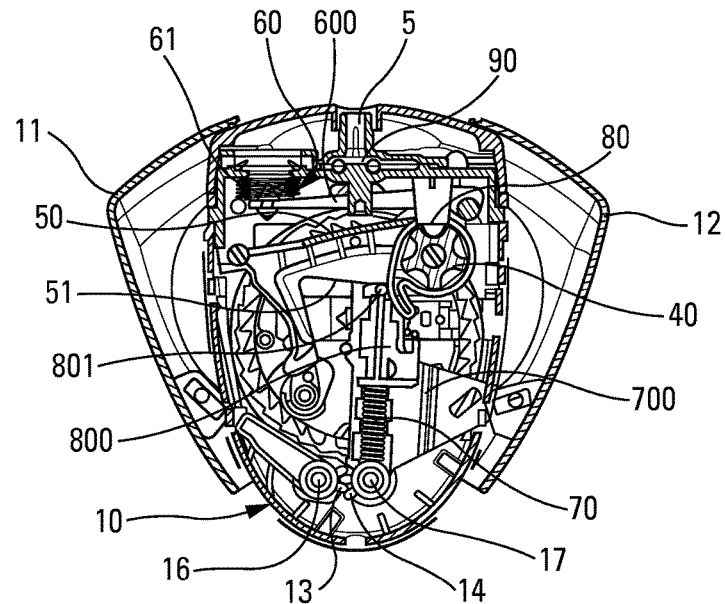

FIGS. 1 to 3 show an advantageous embodiment of a dry-powder inhaler. The inhaler includes a body 10 on which there can be slidably mounted two cover-forming portions 11, 12 that are adapted to be opened so as to open and prime the device. The body 10 can be approximately rounded in shape, as shown in the figures, but it could be of any other appropriate shape. The body 10 includes a mouthpiece or inhalation piece 5 that defines a dispenser orifice through which the user inhales while the device is being actuated. The orifice is typically arranged approximately at the center of the top portion of the body (in the position shown in the drawings). The covers 11, 12 can open by pivoting about a common pivot axis, or about two parallel axes by being meshed together. Any other opening means for opening the device can be envisaged. In a variant, the device could include only a single cover instead of two.

Inside the body 10 there is provided a strip (not shown for the sake of clarity) of individual reservoirs, also known as blisters, said strip being made in the form of an elongate strip on which the blisters are disposed one behind another, in manner known per se. The blister strip is advantageously constituted by a base layer or wall that forms the cavities receiving the doses of powder, and by a closure layer or wall that covers each of said blisters in sealed manner. Before first use, the blister strip can be rolled-up inside the body 10, preferably in a storage portion, and first strip displacement means 40, in particular rotary means, are provided for progressively unrolling the blister strip and for causing it to advance. Second displacement means 50, in particular means that are mounted to pivot on the body 10, are provided for bringing a respective blister into a dispensing position each time the device is actuated. The second displacement means are advantageously mounted to pivot between a non-dispensing position and a dispensing position in which a blister co-operates with said opening means. The strip portion including the empty blisters is advantageously adapted to be rolled-up at another location of said body 10, preferably a reception portion, as described in greater detail below.

The inhaler includes blister opening means 80 (shown in part only for the sake of clarity) preferably comprising a perforator and/or cutter needle for perforating and/or cutting the closure layer of the blisters. Preferably, the opening means comprise a perforator element 80 that is stationary relative to the body 10, and against which a respective blister is displaced on each actuation by the second displacement means. The blister is thus perforated by said perforator element that penetrates into said blister so as to expel the powder by means of the user inhaling. Advantageously, the perforator element is adapted to cut a closure wall of the reservoir in such a manner that the cut portion(s) does/do not obstruct the opening(s) that is/are formed. Documents WO 2006/079750 and WO 2009/007640 describe such blister opening means, and they are thus incorporated in the present description by way of reference.

The first displacement means 40 are adapted to cause the blister strip to advance after each inhalation of the user. The second displacement means 50 are adapted to displace the blister to be emptied against said opening means during actuation, before each inhalation. The second displacement means can be urged by a resilient element 70, such as a spring or any other equivalent resilient element, said resilient element being suitable for being prestressed while the device is being opened. Preferably, the first displacement means 40 are formed by an indexer wheel that receives and guides the blister strip. The description below is thus made with reference to such an indexer wheel 40. Turning the indexer wheel 40 causes the blister strip to advance. Before each inhalation, a full blister is always in a position facing the opening means 80. The second displacement means 50 can include a pivot member that is mounted to pivot about a pivot axis, said indexer wheel 40 advantageously being rotatably mounted on said pivot member.

An actuation cycle of the device can be as follows. During opening of the device, the two cover-forming lateral portions 11, 12 are moved away from each other by pivoting about the body so as to open the device and thus spring-load the device. In this position, the indexer wheel 40 cannot be displaced towards the perforator element 80, since the second displacement means 50 are held by appropriate blocking means (not shown for the sake of clarity). Documents WO 2009/077700 and WO 2009/136098 describe such blocking means, and they are thus incorporated in the present description by way of reference. While the user is inhaling through the mouthpiece, the blocking means are unblocked, thereby causing said indexer wheel 40 to move towards the needle, and thereby causing a blister to be opened.

As explained above, it is desirable for the opening means to be actuated by the user inhaling. In order to trigger the opening means by inhalation, an inhalation trigger system 60 is provided that advantageously comprises an air chamber 61 that is deformable under the effect of inhalation, the air chamber being adapted to release the blocking means. The air chamber 61 may advantageously be made in the form of a bellows. Inhalation by the user causes said deformable air-chamber to deform, thereby releasing said blocking means and enabling the second displacement means to be displaced, and therefore enabling a respective blister to be displaced towards its opening position. The blister is therefore opened only on inhalation, such that it is emptied simultaneously. Thus, there is no risk of any of the dose being lost between opening the blister and emptying it.

The inhaler further includes a dispenser or dispersion chamber 90 for receiving the dose of powder after a respective blister has been opened. The dispenser chamber is advantageously provided with at least one and preferably more beads 91 that are displaced inside said chamber 90 during inhalation, in particular so as to improve dispensing of the air and powder mixture after a blister has been opened, in order to increase the effectiveness of the device.

It can be advantageous for the opening means, in particular for the perforator element, to be formed directly on said dispenser chamber, e.g. at the end of a channel 95 leading to said chamber 90.

After inhalation, when the user closes the device, all of the components return to their initial, rest positions. The device is thus ready for a new utilization cycle.

In an advantageous aspect of the inhaler, the blisters are formed on a flexible elongate strip that, initially, is mainly stored in the form of a roll in a storage housing inside the body 10 of the device. Advantageously, the rolled-up blister strip is held by inner walls of said storage housing without its rear end (rear in the advancement direction of the blister strip) being fastened relative to said body 10, thereby enabling the blister-strip roll to be assembled more easily inside the device. The blister strip is displaced by means of the indexer wheel 40 that advantageously presents at least one and preferably more recesses, each having a shape that corresponds to the shape of the blisters. Thus, when the indexer wheel 40 turns, it causes the blister strip to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of sprocket wheels co-operating with said holes.

After opening one or more blisters, the blister-strip portion with the empty blisters must be suitable for being stored in easy and compact manner in the device, while avoiding any risk of blockage. Advantageously, the used blister strip is rolled-up automatically, once again forming a roll.

In still another aspect of the inhaler, a dose counter or indicator device (not shown for the sake of clarity) is also provided. The device may include numbers or symbols that are marked directly on the blister strip, and that are visible through an appropriate window in the body 10 of the device. In a variant, it is possible to envisage using a counter with one or more rotary disks or rings including numbers or symbols. Documents WO 2008/012458 and WO 2011/154659 describe such counters, and they are thus incorporated in the present description by way of reference. An object of the invention is to avoid counting doses that have not been dispensed, e.g. in the event of a manipulation error, or of an incomplete manipulation of the device. It is thus desirable that the counter or indicator is actuated only once the user has inhaled, since it is this inhalation that makes it possible for the blister to open and the dose contained therein to be dispensed. Advantageously, the counter is thus actuated after inhalation, when the user closes the device.

FIGS. 1 to 3 show an opening and inhalation cycle of the device.

The movable cover element 12 is secured to a cocking member 800 that can slide in an appropriate housing 710. The cocking member 800 thus advantageously pivots relative to said body 10 together with the cover element 12. The cocking member 800 may be moved against the spring 70, advantageously a coil spring, that is arranged in said housing 710. The cocking member 800 is thus connected at one end to said spring 70, and at the other end it co-operates with the second displacement means, in particular with a pivot member 50 that is mounted to pivot on the body 10, and on which the indexer wheel 40 is fastened is rotary manner.

When the movable cover element 12 is opened, as shown in FIG. 1 (closed position) and in FIG. 2 (open position), the cocking member 800 is displaced in its housing 710 by compressing the spring 70. The pivot member 50 of the second displacement means is itself prevented from moving by the above-mentioned blocking means that are released only at the moment of inhalation. Thus, in the absence of any inhalation in the open position in FIG. 2, closing the cover elements 11, 12 would merely cause the cocking member 800 to return to its rest position and the spring 70 to decompress.

Thus, by opening the inhaler, the user primes the system (FIGS. 1 and 2). If the user does not inhale and closes the inhaler, said inhaler merely returns to its start position without displacing the blister strip or the blocking means. There is thus no risk of a blister (and thus an active dose of substance) being lost by accidental or incomplete actuation in which the user does not inhale between opening and closing.

Opening the blister, emptying it, dispensing the powder into the lungs of the user, displacing the blister strip to bring a new full blister to face the opening means, and counting the dose are thus possible only if the user inhales.

The blocking means that block the second displacement means and in particular the pivot member that co-operates with the cocking member, are connected to the deformable air chamber 61 that is sensitive to the user inhaling, so that while the user is inhaling, said deformable air chamber deforms, causing said blocking means to be released. This enables said second displacement means to be displaced towards their dispensing position under the effect of the force exerted by the compressed spring 70 on the cocking member 800 that pushes against the pivot member 50. Such displacement causes a full blister to be opened and a dose to be dispensed.

Said movable cover element 12 is connected to a housing element 700, advantageously via an opening 18 that may be oblong or elongate in shape and in which there is received a lug 718, or the like, of said housing element 700.

Advantageously, the housing element 700 is pivotally mounted on the body 10 about a pivot axis. The housing element 700 includes a housing 710 that receives the spring 70. The spring 70 co-operates with the cocking member 800.

A cam surface 51 is formed on said movable support means 50, on which the cocking member 800 slides. While the housing element 700 is being displaced about its pivot axis during displacement of the movable cover element 12, the cocking member 800 is thus adapted to compress the spring 70 when the cover element 12 is open, and to decompress said spring 70 when said cover element 12 is closed.

Advantageously, in its portion in contact with the cam surface 51, the cocking member 800 includes a rounded portion 801, such as a ball-shaped end, so as to make it easier for the cocking member 800 to slide over said cam surface 51.

In this embodiment, the movable support means are made in the form of a member 50 that is pivotally mounted on the body 10 about a pivot axis 511. Since the above-mentioned cam surface 51 is formed on said pivot member 50, when the spring 70 is loaded while the movable cap element 12 is opening, said pivot member 50 is urged towards its dispensing position by said cocking member 800 and the spring 70 is compressed.

After inhalation, i.e. in the dispensing position, the blocking means have been released, and the movable support means 50 have been displaced upwards by the compressed spring 70.

In addition, after inhalation and thus displacement of the movable support means 50 towards the dispensing position, closure of the movable cover element 12 returns the housing element 700 towards its start position.

Advantageously, the two movable cover elements 11, 12 mesh together via appropriate gearing 13, 14 so as to guarantee symmetrical opening and closing of said two movable cover elements. They can mesh together in the proximity of their pivot axes 16, 17.

In the invention, said cocking member 800 and said resilient means 70 are assembled in said housing 710 provided in said housing piece 700 connected to a cover element 12.

Figure 10:
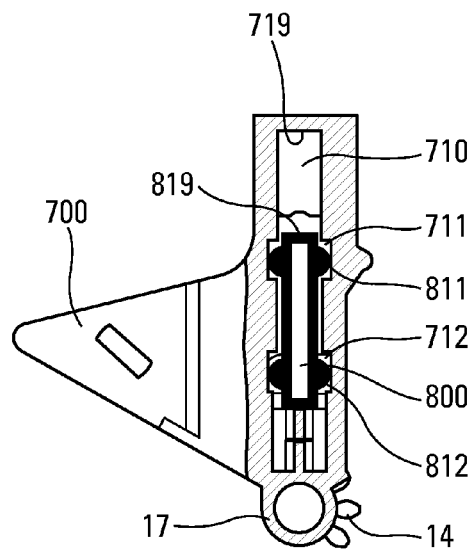
FIGS. 10 to 13 are diagrammatic and fragmentary cross-section views showing the assembly stage for assembling the cocking member and the loader spring in the housing of the housing piece.

Advantageously, on each side, said housing 710 includes side rails 713, 714 that are interrupted by side openings 711, 712. The cocking member 800 includes side projections 811, 812 that are adapted to co-operate with said side openings 711, 712 so as to enable said cocking member to be assembled in said housing 710. The side rails 713, 714 co-operate with said side projections 811, 812 of said cocking member 800 so as to enable said cocking member to slide in said housing 710, while holding said cocking member in said housing. When the side projections 811, 812 of the cocking member 800 are level with the side openings 711, 712, said cocking member may be inserted into the housing 710, as can be seen in FIGS. 8 and 10. Once the cocking member has slid in said housing from its insertion position, as can be seen in FIGS. 11 to 13, said side projections 811, 812 are blocked by said side rails 713, 714, and this enables the cocking member to slide in the housing while preventing the cocking member from leaving said housing.

Advantageously, said side openings 711, 712 of the housing 710 co-operate with said side projections 811, 812 of the cocking member merely in the assembly position of the cocking member, said resilient means 70 urging said cocking member out of said assembly position. The resilient means preferably comprise a coil spring that is arranged in said housing 710, as can be seen in FIGS. 7 and 11 to 13.

Figure 11:
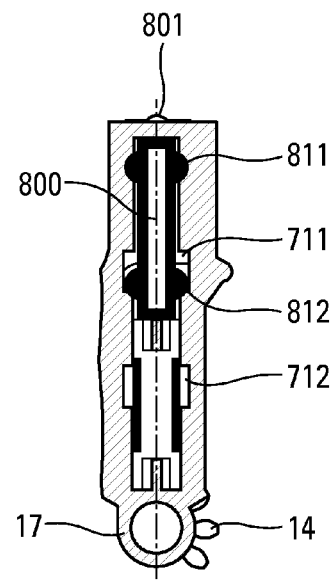
Figure 12:
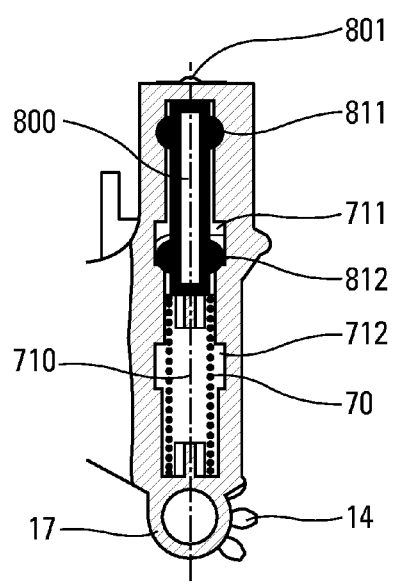
Figure 13:
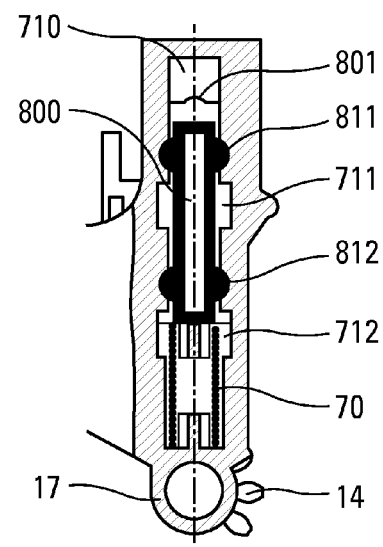

FIGS. 10 to 13 show assembly of the cocking member 800 in the housing 710. As explained above and as can be seen in FIGS. 8 and 10, the cocking member 800 is placed above the housing 710 with the side projections 811, 812 facing the side openings 711, 712 of the housing. The cocking member may then be inserted into the housing 710. After its insertion, the cocking member 800 is moved by sliding in the housing so as to bring a leading end 819 of the cocking member 800 into abutment with an end edge 719 of the housing 710, as can be seen in FIG. 11. The resilient means 70, specifically a coil spring, are then inserted into the housing 710 in their compressed state at the end remote from said leading end 819 of the cocking member, and when the spring is released from its compressed condition, it co-operates with said cocking member 800 so as to urge it resiliently towards its abutment position, as can be seen in FIG. 12. When the cocking member 800 slides in the housing 710 away from its abutment position, it thus compresses said spring, and this makes it possible to ensure that the device operates.

Advantageously, after inserting the spring in the housing 710, the cocking member 800 can no longer reach its insertion position in FIG. 10. FIG. 13 shows the position in which the cocking member has been moved as far as possible in the housing, with the spring completely compressed. It should be observed that the side projections 811, 812 can no longer reach the side openings 711, 712 and there is thus no risk of the cocking member leaving the housing 710 after the spring has been assembled. This guarantees that the dispenser operates reliably. The robustness of the device is reinforced by the absence of adhesively-bonded, heat-sealed, or clipped parts for holding the cocking member in the housing. Since the forces created by this type of cocking and actuation system for an inhaler are very substantial, the notion of robustness is particularly important for the reliability of the device. In addition, the component parts of the system, in particular the cocking member 800 and the housing piece 700 with its housing 710 are simple to mold, and this makes manufacture and assembly easier and less costly.

In all of the above-described embodiments, the blister strip is formed by a strip that presents two ends. In a variant, a continuous strip could be used. Other modifications are also possible without going beyond the ambit of the present invention.

The present invention therefore makes it possible to provide a dry-powder inhaler that provides the following features:

a plurality of individual doses of powder stored in individual sealed blisters, e.g. 30 or 60 doses stored on a rolled-up strip;

the powder is released by perforation that is achieved by the user inhaling, the blister being perforated by means of an inhalation detector system that is coupled to a prestressed release system;

appropriately-shaped drive means that are engaged with blisters so as to displace the blister strip after each inhalation, and bring a new full blister into a position in which it is to be opened by appropriate opening means;

means for avoiding doses being lost in the event of the inhaler being opened, but in the absence of any inhalation; and a dose indicator adapted to count the doses only in the event of inhalation.

Other features are also provided by the device of the invention as described above.

It should be observed that the various features, even if they are shown as being provided simultaneously on the inhaler, could be implemented separately. In particular, the inhalation trigger mechanism could be used regardless of the type of reservoir opening means, regardless of the use of a dose indicator, regardless of the way in which the individual blisters are arranged relative to one another, etc. The cocking means and the inhalation trigger system could be made in some other way. The same applies for other component parts of the device.

Various modifications are also possible for the skilled person without departing from the scope of the present invention as defined in the accompanying claims. In particular, the various characteristics and functions of the device described with reference to the drawings can be combined together in any appropriate manner.

The invention claimed is:

1. A fluid dispenser device including a body and at least one cover element that is mounted to pivot on said body between a closed position and an open position, said device including individual reservoirs, each containing a single dose of fluid, opening means being provided for opening one of the individual reservoirs each time the device is actuated, said device including movable support means that are adapted to move one of the individual reservoirs against said opening means on each actuation, said movable support means being displaceable between a non-dispensing position and a dispensing position, said movable support means being urged towards their dispensing position by resilient means, and being held in their non-dispensing position by blocking means that are released by the user inhaling, said device including a cocking member that co-operates with said resilient means and with a cam surface that is formed on said movable support means, wherein said cocking member and said resilient means are assembled in a housing provided in a housing piece located within the body; and wherein on each side, said housing includes side rails that are interrupted by side openings, said cocking member including side projections that are adapted to co-operate with said side openings so as to enable said cocking member to be assembled in said housing, said side rails co-operating with said side projections of said cocking member so as to enable said cocking member to slide in said housing, while holding said cocking member in said housing.

2. The device according to claim 1, wherein said side openings co-operate with said side projections solely in an assembly position of said cocking member, said resilient means urging said cocking member out of said assembly position.

3. The device according to claim 2, wherein said resilient means comprise a coil spring that is arranged in said housing.

4. The device according to claim 1, wherein said movable support means support a guide wheel, the individual reservoirs being made in the form of an elongate strip comprising the individual reservoirs disposed one behind another, said guide wheel causing said strip to advance each time the device is actuated.

5. The device according to claim 1, wherein said opening means-include a perforator element that is adapted to cut a closure wall of the reservoir in such a manner that the cut in the closure wall does not obstruct the opening that is formed.

6. The device according to claim 1, including an inhalation piece-and an inhalation trigger system that comprises a deformable air chamber that co-operates with said inhalation piece, and a trigger element that co-operates with said air chamber, such that during inhalation through said inhalation piece, said air chamber is deformed and said trigger element actuates said opening means, such that the individual reservoirs are opened in turn by said opening means.

7. The device according to claim 1, wherein the fluid is a powder.

8. The device according to claim 1, wherein said resilient means is a spring or a spring blade.

9. The device according to claim 1, wherein the housing piece is connected to the at least one cover element.

10. The device according to claim 1, wherein the side projections pass through said side openings during assembly and said side rails co-operate with said side projections after assembly.

* * * * *